US008346388B1

(12) United States Patent
Tritz

(10) Patent No.: US 8,346,388 B1

(45) Date of Patent: Jan. 1, 2013

(54) SYSTEM AND METHOD FOR AUTOMATED TACTILE SORTING

(75) Inventor: Jared Michael Tritz, Vesper, WI (US)

(73) Assignee: Jared Michael Tritz, Vesper, WI (US)

( * ) Notice: Subject to any disclaimer, the term of this patent is extended or adjusted under 35 U.S.C. 154(b) by 987 days.

(21) Appl. No.: 12/316,753

(22) Filed: Dec. 15, 2008

Related U.S. Application Data

(60) Provisional application No. 61/014,035, filed on Dec. 15, 2007.

(51) Int. Cl.
*G01N 33/02* (2006.01)

(52) U.S. Cl. ........ 700/230; 700/213; 700/219; 700/223; 209/590; 209/672; 73/81; 73/579; 426/231

(58) Field of Classification Search .................. 700/230
See application file for complete search history.

(56) References Cited

U.S. PATENT DOCUMENTS

| | | | | | |
|---|---|---|---|---|---|
| 3,627,126 | A | * | 12/1971 | Fitzgerald et al. | 209/41 |
| 3,750,127 | A | * | 7/1973 | Ayers et al. | 340/665 |
| 3,773,172 | A | * | 11/1973 | McClure et al. | 209/565 |
| 3,903,733 | A | | 9/1975 | Murayama et al. | |
| 3,973,150 | A | | 8/1976 | Tamura et al. | |
| 4,055,842 | A | | 10/1977 | Yakshin et al. | |
| 4,061,020 | A | | 12/1977 | Fridley et al. | |
| 4,106,628 | A | | 8/1978 | Warkentin et al. | |
| 4,131,012 | A | | 12/1978 | Courtiol | |
| 4,164,291 | A | * | 8/1979 | Carlow | 198/349.95 |
| 4,216,403 | A | | 8/1980 | Krempl et al. | |
| 4,279,346 | A | * | 7/1981 | McClure et al. | 209/582 |
| 4,299,326 | A | * | 11/1981 | Ulch | 209/564 |
| 4,491,760 | A | | 1/1985 | Linvill | |
| 4,884,696 | A | * | 12/1989 | Peleg | 209/545 |
| 4,901,861 | A | * | 2/1990 | Cicchelli | 209/539 |
| 5,152,401 | A | * | 10/1992 | Affeldt et al. | 209/556 |
| 5,372,030 | A | | 12/1994 | Prussia et al. | |
| 5,544,761 | A | * | 8/1996 | Zdroik | 209/672 |
| 5,811,680 | A | * | 9/1998 | Galili et al. | 73/579 |
| 5,813,542 | A | | 9/1998 | Chon | |
| 5,862,919 | A | | 1/1999 | Eason | |
| 6,125,686 | A | * | 10/2000 | Haan et al. | 73/12.09 |
| 6,240,766 | B1 | * | 6/2001 | Cawley | 73/12.01 |

(Continued)

OTHER PUBLICATIONS

BBC Technologies Ltd Soft Sorta 2 Pages South Haven, MI 49090 USA.

*Primary Examiner* — Gene Crawford
*Assistant Examiner* — Kyle Logan
(74) *Attorney, Agent, or Firm* — Jelic Patent Services, LLC; Stanley E. Jelic

(57) ABSTRACT

A system and method for automated piezoelectric sensor-based tactile sorting of plurality of small objects. A high accuracy, high precision delivery system targets the sensor which accounts for softness and mass of individual objects by measuring a force exerted and total contact time for each object upon passing contact with a sensing surface of a piezo sensor, wherein a plurality of objects cascade onto the sensor in one-by-one fashion. The quantified force and contact time values are then analyzed and compared against two threshold values or a range of threshold values which are predetermined and preset based on data from optimal objects and undesirable objects or possibly a spectrum of objects which has been analyzed and recorded to assist in calibrating the system.

14 Claims, 8 Drawing Sheets

U.S. PATENT DOCUMENTS 6,390,915 B2 5/2002 Brantley et al.
6,435,002 B1 * 8/2002 Briggs ........................... 73/23.2
6,539,781 B1 * 4/2003 Crezee .............................. 73/81
6,553,814 B2 * 4/2003 de Greef ........................... 73/81
6,643,599 B1 * 11/2003 Mohr et al. ................... 702/108
6,857,317 B2 * 2/2005 Sakurai ........................... 73/579
6,998,559 B2 * 2/2006 De Baerdemaeker et al. ............................. 209/590
2005/0266967 A1 * 12/2005 Considine et al. .............. 482/84
2006/0186307 A1 * 8/2006 Pletner et al. ................. 248/550
2008/0003333 A1 * 1/2008 Furniss ......................... 426/231
2008/0156098 A1 * 7/2008 Vetelino et al. ................. 73/579

* cited by examiner

Fig. 4A
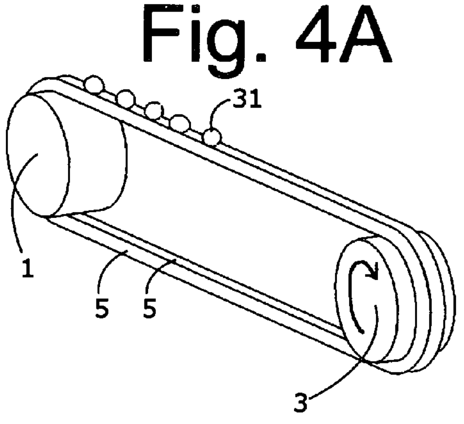
Fig. 4B
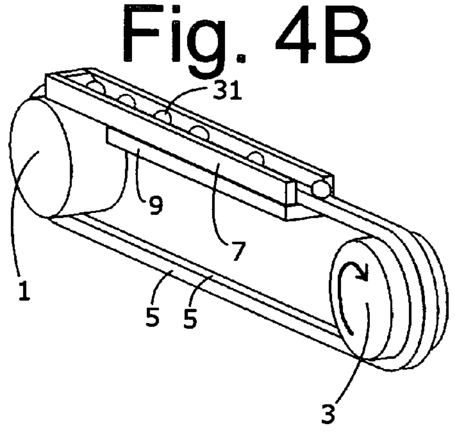
Fig. 4C
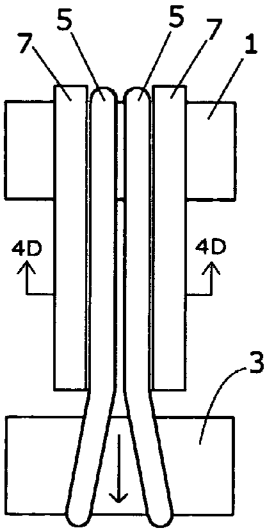
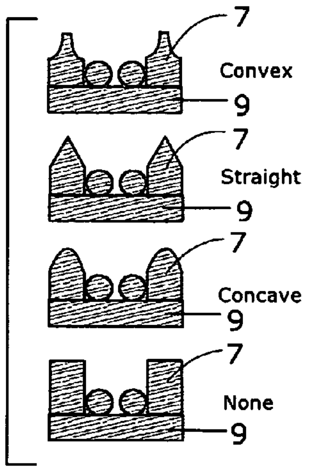
Fig. 4D
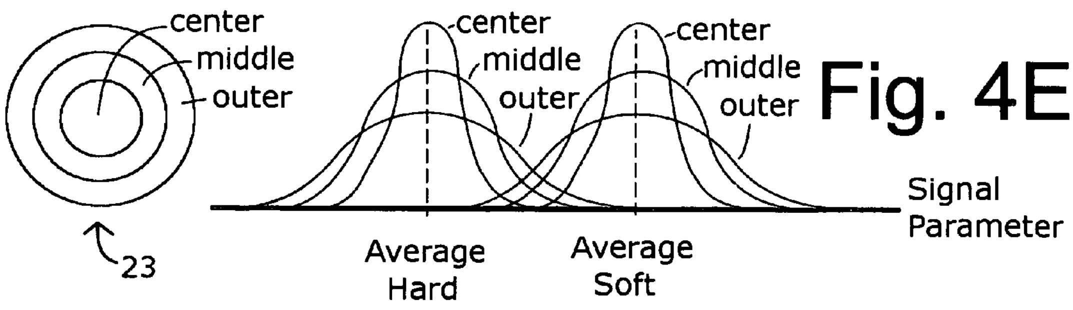
Fig. 4E Fig. 5A
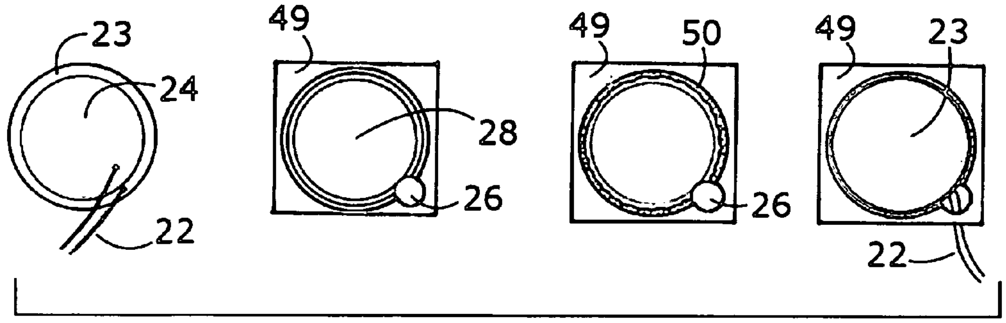
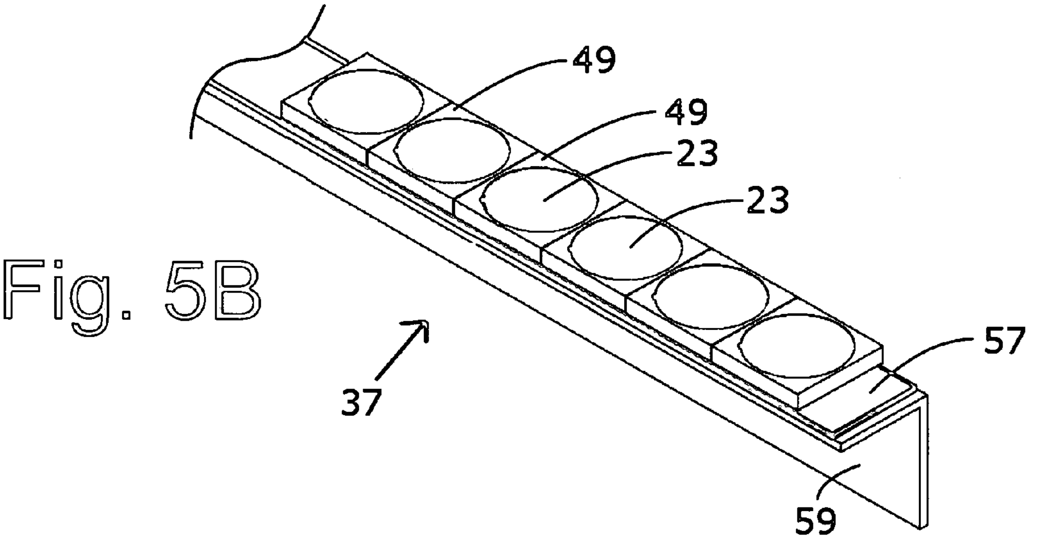
Fig. 5B
Fig. 6A
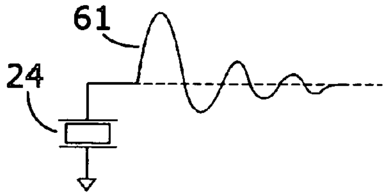
Fig. 6B
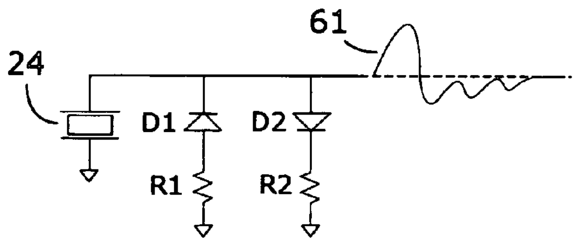

SYSTEM AND METHOD FOR AUTOMATED TACTILE SORTING

CROSS-REFERENCE TO RELATED APPLICATION

This non-provisional patent application claims priority under 35 USC 119(e) to the U.S. provisional patent application, Ser. No. 61/014,035 filed Dec. 15, 2007, the disclosure of which is incorporated by reference.

FIELD

The present technology relates in general to an automated, sensor-based, tactile sorter of small objects and, specifically, to a system and method for an automated piezoelectric sensor-based sorter for sorting of small objects based on an individual object's, such as cranberry, softness.

BACKGROUND

Cranberries, by way of example, are a major commercial crop in the United States. Grown traditionally on a flat parcel of land the vines will cover the ground forming so called cranberry beds. The small, red football-like shaped fruit appears on short upright branches several inches above the ground and is harvested in the fall before freezing. Various mechanisms such as freezing, insect damage, physical damage due to harvest, etc. may weaken the fruit and cause it to become susceptible to bacteria, decay, and early spoilage. When selling fresh cranberries it is desirable to present only unspoiled berries. Spoiled berries not only deter consumers but also cause sanitary issues in shipping and display because sticky juices from decaying fruit will leak onto containers, shelves and equipment. Softness and reduced structural integrity of the fruit is indicative of spoilage.

Cranberries intended for sale as fresh fruit are handled carefully after harvesting. They are taken to receiving stations where they are cleaned and stored prior to packaging. Just prior to packaging the fruit is sorted to remove spoiled berries and then placed in distributable containers. Various degrees of sorting are also performed to remove spoiled berries in what is considered upgraded fruit, sold as baking ingredients for example. Cranberries intended for juicing are typically least sorted.

For small operations sorting fresh cranberries can be an important way to add value to a limited crop volume as the price per pound is higher than for juice berries. Sorting can be done manually but is often augmented by a machine or some type of automation. For larger operations there is generally a greater reliance on automation.

While manual sorting can be important as a final check to automated sorting, reliance on manual sorting to remove the bulk of spoiled fruit is slow and unreliable. Manual sorting usually depends on a multitude of variables associated with an individual human sorter. In agriculture, an individual human sorter may employ multi-sensory functions, such as vision, touch, smell, hearing, and taste to examine the quality of a product. However, the manual sorting can vary widely from individual to individual, which introduces unwelcome fluctuations in the end product's quality. The length of the sorting time may also play a role. Manual sorter's ability could be affected by time of day or night, feeling tired or rested, quality of vision and touch. Physical and emotional states, judgment, and human reliability can have a detrimental impact on the end product. Overall, manual sorting of large quantities of small objects tends to be expensive and inefficient. Also, finding and employing steady seasonal workers can be a significant hurdle. As the product's quality and quantity are affected by and remain vulnerable to manual labor's multi-factor fluctuations, farmers, food, and drink producers seek other solutions. To limit dependency on manual workers, to preserve qualitative consistency, to increase processing rate, quality and quantity of throughput, automated sorters, also known as separators, are increasingly utilized.

Various sorting techniques have been used to assist in the automated sorting of cranberries for removal of spoiled berries. The techniques could be classified loosely in two categories as 1) using mechanical probing mechanisms and 2) using optical probing mechanisms. Mechanical sorting mechanisms disclosed to date employ a variety of techniques to remove rotten, soft, or undesirable berries. The techniques include: a) "Bailey Mills" which sort by bouncing the fruit over a small hurdle and measure the fruit's elasticity without accounting for rigidity, b) "Puff Ball" machines which attempt to push fruit through a small opening and measure the fruits rigidity without measuring elasticity. Such rough handling of fruit compromises the quality of the end product even for initially high quality berries which pass the sorter. Thus this method is undesirable to use for fresh packaging where even good fruit becomes damaged due to the sorting process' mechanism. c) "Tactile Sorting" machines which employ a force transducer to create an electrical signal and then process the signal electronically and decide whether the fruit should be removed.

References exist for tactile sorting techniques using piezo transducers under various configurations, which bring a mobile sensor into contact with the object under test but none disclose a method for delivering the objects to a stationary sensor. Also, none disclose a method of processing signals to account for an objects elasticity and rigidity simultaneously using either analog or digital electronics.

Piezoelectric or piezo sensors are electromechanical systems that react to compression. The word "piezo" is derived from the Greek "piezein," which means to squeeze or press. The piezoelectric effect finds useful applications such as the production and detection of sound, generation of high voltages, electronic frequency generation, microbalances, and ultra fine focusing of optical assemblies. The piezoelectric effect has further found a sorting application.

Piezoelectricity is the ability of some crystals and ceramics to generate an electric potential in response to applied mechanical stress. Piezoelectric sensors convert pressure, acceleration, strain, or force to an electrical signal. When pressure or touch is exerted upon a piezo sensor, a separation of electric charge across the crystal lattice occurs and can be measured as voltage potential. Piezo sensors show almost zero deflection with a high natural frequency and an excellent linearity over a wide amplitude range. Piezoelectric technology is insensitive to electromagnetic fields and radiation, enabling measurements under harsh conditions. The high modulus of elasticity of many piezoelectric materials is comparable to that of many metals. The piezoelectric effect is reversible, meaning, materials exhibiting a direct piezoelectric effect, that is, the production of electricity when stress is applied; also exhibit a converse piezoelectric effect, the production of stress or strain when an electric field is applied.

Although primarily described in an agricultural context, and in particular the embodiment of cranberry sorting system, such a sorting system could apply not only to a variety of other fruits and vegetables but also to any other field where sorting of small objects, based on a objects physical structure, namely elasticity and rigidity is desired.

SUMMARY

In a common embodiment of a sorting system objects enter the sorting system and are brought into contact with a surface moving at a constant velocity with respect to the machine. Objects come to rest with respect to the surface and thus obtain a constant velocity as they move through the machine. This can assist in aligning the objects with fixed sensors and/or actuation devices as those familiar with Newtonian mechanics will recognize since the objects traveling at a constant velocity will follow a predictable path until acted upon by an unbalanced force.

This embodiment is used in sorting machines to achieve predictable freefall trajectories of objects being sorted. The metrics for success of a particular implementation of this technique include but are not limited to: 1) How many objects can be processed per unit time, 2) Are the objects ordered in more than one dimension, i.e. is it aligned in rows along the moving surface. 3) How small is the standard deviation of the objects velocity vector at the position where an important measurement and/or actuation is to occur.

In one embodiment the delivery method optimizes for the success of a tactile sorting system where the objects are brought into contact with the stationary sensing surface. Often such sensors will have a diminished or degraded electrical response if the contact point between the sensor and object move away from the sensors optimal sensing location. This is true of piezo based sensing transducers however the reasoning will not be elaborated on in this document.

In another embodiment a moveable surface comprising round belts and rollers adjacent to an immovable one comprised in one embodiment of a plastic board and plastic fins. These are used together in a unique way such that the immovable surface supports and guides the moveable one giving it stability while the shape of the immoveable one and relative motion of the belts sliding along it assists in settling objects quickly and into tightly packed single file rows at rest with the movable surface. Lastly the spacing of fins on the immovable surface and spacing of groves on the rollers assist in shaping the belts to avoid any pinching or gripping between the objects and the belts at the drop off point providing a more consistent release where objects leave the movable surface and continue in free fall toward the tactile sensing surface.

In another embodiment a plurality of sensing surfaces are arranged to test a plurality of objects simultaneously. In this embodiment there is a plurality of belt pairs running parallel to each other in a plurality of channels forming rows. All of the components of a row necessary for sorting, which includes the electronics, are collectively referred to here as a lane. Each lane is identical in function to the other lanes and each forms an individual pathway capable of sorting objects.

Various embodiments exist for interpreting the signal created by the sensor when an object bounces off the sensing surface. In most cases the sensing surface and raw signal will behave like a damped oscillator when impacted by the object where only the first half cycle of the first oscillation is of interest as this is the time when the object is coupled to the sensor; while the secondary oscillations are not of interest since this is the time when the sensor tends to oscillate at it's natural frequency. In all cases it is of interest to have the sensor and sensor signal quickly return to the initial state and be ready for measuring another object as soon as the first half cycle of the first oscillation are complete. In one embodiment the signal conditioning circuit forces the electrical signal to a reset state even before the sensor itself fully recovers. Forcing the signal back to a reset state in an appropriate way can eliminate secondary oscillations of the signal which simplifies signal processing significantly.

In one embodiment when an object impacts the sensing surface the surface it is stressed by the impact and the stress translated to a piezo crystal which is glued to the sensing surface. The piezo's signal is processed electronically to determine the duration of the objects impact, in other words the time between first contact and total rebound. The duration of object to sensor contact is compared to a preset threshold value. In some embodiments this could be a single value threshold and in some embodiments it could be a multiple range based decision whether to divert the object. In this embodiment the contact time is used to correlate with a physical property or properties of the object, for example rigidity.

In a further embodiment when an object impacts the sensing surface the resilient surface is temporarily deformed by the impact. In this embodiment if deformation is translated to a piezo crystal which is glued to the sensing surface then the piezo's signal is processed electronically to determine the maximum deformation of the surface which corresponds to the piezo signals peak voltage. This value might be compared to a threshold value or in some embodiments a multiple range of values used to make an actuation decision. In this embodiment the deformation is proportional to the force exerted by the object as it rebounds and can be correlated with physical properties of the object such as mass.

In another embodiment both the contact time and the maximum deformation are used to make an actuation decision. In this embodiment it is possible to compensate for the fact that two objects might have the same contact time for different reasons, for example in one instance it could be due to lack of rigidity and in another instance it could be due to it having more mass than the first. Accounting for both peak deformation and contact time at once in making an actuation decision allows the sorter to decide for example to remove an object with too long of contact time when it's peak force is low, whereas in another case it might not eject an object with the same contact time because it's peak force was also high meaning more of the contact time could be attributed to mass.

In yet another embodiment the invention could be used to record many measurements very quickly and thus gather statistics for a large population of small objects. For example, in one embodiment where the primary variable of interest among objects is mass a set of preselected objects could be used for calibration and the integral of an objects signal across a constant resistance used to generate a current and correlated the accumulation of charge from that current to a mass for those objects.

In another embodiment the sensing surface is exposed as directly to objects under test to improve signal fidelity. Direct coupling of the object to the sensing surface has been found to produce signals which best reflect object properties. In order to repeatedly expose object directly to a sensing surface and still keep the surface clean, and free of sugary residues for example which further collect dust and debris, the sensors have been covered with a thin sheet of anti-static plastic. The plastic is stretched tight across the sensors and moved continually to maintain a clean consistent coupling between objects and sensors.

A common embodiment of the actuation mechanism for a sorting systems of this type is to reject objects by diverting them with an air stream which deflects them from a trajectory leading to the desirable object group and thus sending the object on an alternate trajectory into a rejection container. It has been found important for various embodiments of the tactile sorter disclosed here to position multiple air jets in such a way as to cover a range of paths which deviate from the average post measurement trajectory. This is to avoid missing the object with the air if it is decided to eject it while the object's bounce was not perfectly straight. Disclosed here is a novel and effective means of constructing an air manifold to serve the purpose of spanning a wide range of angles through which an object may bounce.

Still other embodiments will become readily apparent to those skilled in the art from the following detailed description, wherein are described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF THE DRAWINGS

FIG. 4 is a composition of drawings illustrating the details of the delivery system which improve precision of object trajectories targeting the sensors.

FIG. 5 is a close up diagram showing the piezo sensors secured within mounting blocks and the mounting blocks secured to a sensor mounting bar, of the system of FIG. 1.

FIG. 6 illustrates a signal conditioning circuit used to suppress secondary oscillations of the piezo crystal's electrical output.

DETAILED DESCRIPTION

Although described in this application in relation to an automated piezoelectric tactile sorter primarily intended for sorting of cranberries, the embodiments described apply generally to all forms of sorters capable of sorting small objects based on tactile characteristics, mass, and force exerted by a small object on a the piezoelectric sensor.

Softness of an object can be indicative of other properties of the object. In agriculture, excessive softness can indicate decay. Excessive hardness, on the other hand, can indicate immaturity of an object. Ability to accurately and precisely detect and separate objects based on softness, mass, or density is one of the significant challenges in the food industry.

Figure 1:
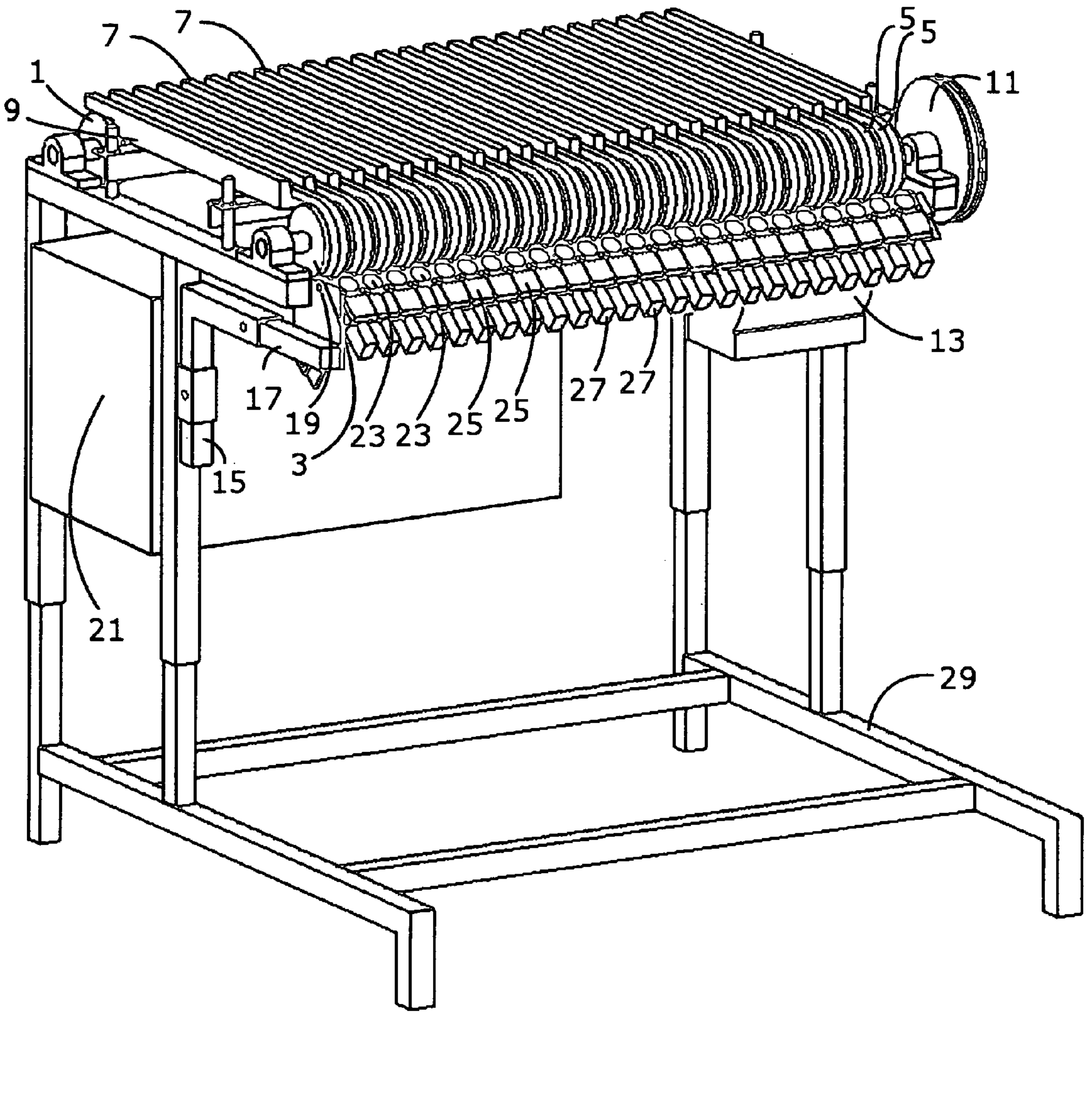
FIG. 1 is a functional diagram showing a system for tactile sorting of small objects, in accordance with one embodiment

FIG. 1 is a detailed drawing showing one embodiment a tactile sorting system. The system includes a delivery module comprised of a delivery board 9, fins 7, front roller 3, rear roller 1, delivery belts 5, drive motor 13, drive sheave 11, sensing surfaces 23, actuation air manifolds 25, air valves 27, an electronics housing 21, a frame 29, and some adjustable mechanisms to position the sensors, namely horizontal adjustment 17, vertical adjustment 15, angular adjustment 19.

Figure 2:
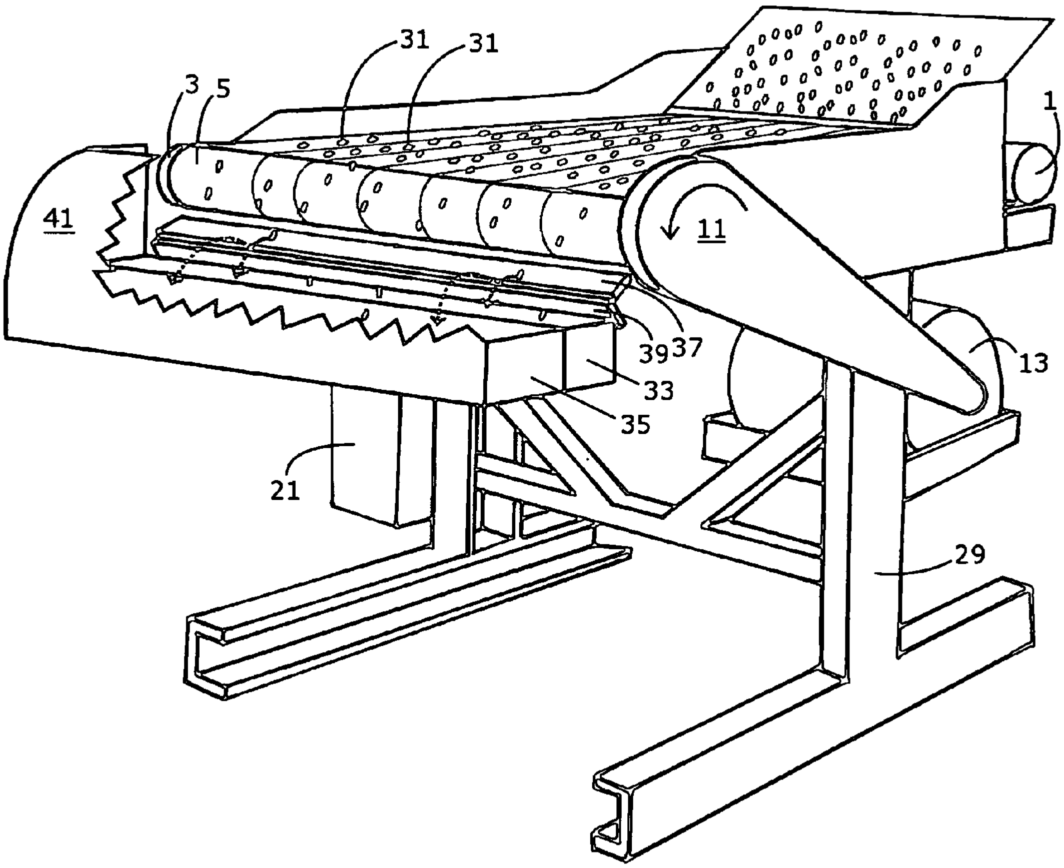
FIG. 2 illustrates the way objects flows through a tactile sorter in contact with a moveable surface, how objects move forward to a drop off point, how objects impacts the sensors, and are either deflected by an air jet or follow a natural path.

FIG. 2 illustrates another embodiment of a tactile sorting system where the delivery surface comprises one or more belts 5 guided by two rollers 1, 3. Objects 31 flow forward on the horizontal delivery surface. Objects leave the delivery surface at a drop off point and impact a sensor module 37. After rebounding from the sensor module objects pass over an actuation module 39. If the actuation module does not act on the object the object will land in the accepted bin 33. If the actuation module does act on the object the object is deflected with an air burst into a rejected bin 35. A hood 41 assists in channeling deflected objects into the rejection bin.

Figure 3:
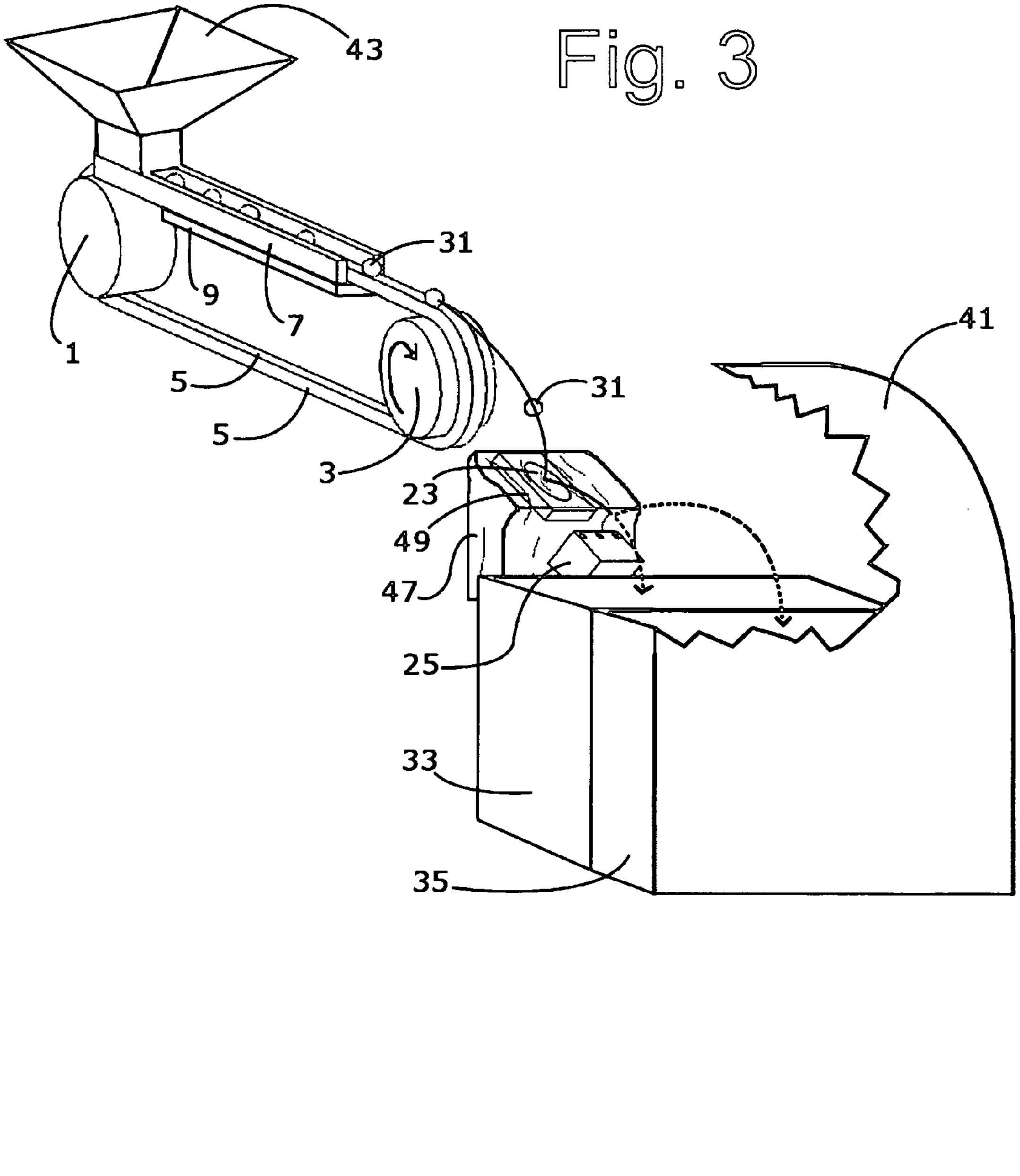
FIG. 3 is a simplified drawing showing relative placement of physical components of a single lane, of the system of FIG. 1.

FIG. 3 illustrates an embodiment of a tactile sorter comprising a single lane. Objects are fed in through the funnel 43, move forward on the delivery belts 5, leave the surface at a drop off point and travel to impact the sensor surface 23, and then bounce over the actuation air manifold 25.

If the air manifold fires an air jet the object is diverted into the rejected bin 35, and if not then it follows a natural path into the accepted bin 33. In one embodiment the objects are cranberries which tend to bounce sideways. In this embodiment the air manifold has multiple holes so that if the object bounces sideways it still has a possibility to be intercepted.

In one embodiment the objects are berries and tend to deposit a sugary residue. In this embodiment the sensor surface is covered with a thin sheet of plastic FIG. 3, 47 which can be periodically moved or replaced to avoid the accumulation of residue from the objects. In a further embodiment the plastic is weighted on either end to keep it tight over the sensor. In another embodiment the plastic is fed off a roll beneath the sensor.

Objects coming to the edge of the delivery surface are released to target the sensing surface 23. It is best if the objects all follow the exactly the same trajectory and hit the sensor in exactly the same place, however, even when the belts turn at a constant speed the objects will leave the delivery surface at a range of angles. This happens for a multitude of reasons including object stickiness, objects wedging into the belt, misalignment of belts, and objects rolling or failing to come to rest at all before they leave.

Accurate delivery of objects to the sensing surface is imperative to acquiring high fidelity signals from the tactile sensors. In one embodiment of a tactile sensor it is important to impact the sensor in the middle. In this embodiment FIG. 4E illustrates that if the objects impact the sensor 23 at the center then the standard deviation for a set of signal parameters generated by similar objects is smallest. If however the objects impacts the sensor in the outer regions then the standard deviation for a set of signals generated by similar objects is much larger. Since there can easily be overlap between the signals for dissimilar objects it is desirable to reduce the standard deviation in all signals in order to best distinguish between all dissimilar objects.

In most embodiments of the delivery module the belt diameter is preferably small to reduce stretching when the belt travels around the roller. Stretching causes the belt to accelerate at the drop off point as well, which could cause variation in the object's velocity vector as the object leaves the delivery surface.

In a simplified embodiment of the delivery module FIG. 4A shows two round belts 5 running side by side carry objects from the input 43 forward to the drop off point. In an improved embodiment of the delivery module FIG. 4B the delivery board 9, and fins 7 help support the belts which suppress the pressure to spread out from the weight of objects. The front roller 3 and the rear roller may be grooved to assist in guiding the belts. If the roller is not grooved an additional guide (not pictured) is positioned somewhere contacting the belts to guide them.

A further improved embodiment of the delivery system FIG. 4C uses both fins 7, and grooved rollers. In this embodiment wider grooves are placed in the front roller 3, and narrower groves in the rear roller 1. The wider grooves guide the belts 5 slightly wider at the drop off point. Thus at the drop off point the belts move apart slightly so that any gripping of the objects which may have occurred due to settling or wedging in the belts is alleviated before the object reaches the drop off point.

A final embodiment of the fins for this delivery system is shown in FIG. 4D where the fins 7 are given a profile, namely concave, straight, or convex, and square or none. These fin profiles are in the order of the preferred embodiment from top to bottom. All of these fin profiles serve one purpose which is to keep objects from being swept forward until it has settled into single file rows between the belts. In this embodiment of the delivery only the bottom most objects are in contact with both belts and dragged forward. Unsettled objects experience drag from the fins 7 until space opens up for it to enter the single file row in between both belts. Proper profiling keeps objects from becoming wedged when two fit side by side for example or when an anomalously large object enters. Lastly the proper profiling helps stop objects from rolling or bouncing along the top of the fin and not settling in between the fins.

In one embodiment sensing is done with a piezo buzzer element where the objects are given an identical impact velocity and rebound naturally from the sensor surface under their own weight. Signal fidelity is best when objects contact the sensor surface directly without mediating the interaction through a protective layer FIG. 3, 47. However, when the objects are cranberries for example then the impact of thousands and thousands of objects accumulates a sticky residue which will have a negative effect on sensing. Thus it is necessary to use a protective cover for the sensors. In some embodiments a permanent protective layer is used to cover the sensing surface, however a permanent cover requires cleaning.

In the preferred embodiment the sensor surface is kept clean using a thin moveable cover. In some embodiments this is a thin plastic sheet such as painter's drop cloth, saran wrap, or anti-static packaging plastic. In this embodiment continual cycling of a thin protective cover FIG. 3, 47 over the sensors keeps them at peak sensitivity throughout operation. Continual cycling is preferred to a permanent cover layer or even a removable protective cover which has to be cleaned or replaced periodically. Continually cycling a protective layer mitigates the continual degradation of sensitivity which occurs due to collection of residue and debris between cleaning and/or replacement cycles for a permanent cover.

In most embodiments this layer FIG. 3, 47, is a thin soft plastic stretched tight to fit conformably over the sensing surface without wrinkles. Wrinkles degrade sensing. It's recommended that the layer be cycled at a rate such that the sensor surface is completely refinished every 15-30 minutes under normal use. This is to keep sticky residue from collecting and avoid the formation of stretch bubbles due to the abuse of objects bouncing on the soft plastic. Stretch bubbles interfere with sensing so it is desirable to cycle at a rate which is fast enough to avoid them forming.

In the preferred embodiment FIG. 1, the sensing module will accommodate a sheet of plastic 47 being draped over the whole sensing bar 37. In this embodiment the actuation bar is separated from the sensing bar and possibly rotates or slides away from the sensing bar to create space for feeding plastic through. Once the plastic is in place the actuation bar moves close to the sensing bar again leaving just enough room for the plastic to feed through adjacent the air manifold. In the preferred embodiment the plastic sheet is automatically wound off one roll from beneath the sensing bar, up and over the sensing bar, and then wound up on another roll to enable continual reliable cycling of the plastic layer.

In one embodiment FIG. 5A a piezo buzzer element forms the tactile sensor. The sensor surface 23 is a metal disk and the piezo crystal 24 is fixed to the disk. Wires 22 are soldered to these. A mounting block 49 has a pocket 28 machined on one side to accept the sensor and a hole 26 drilled through to let the sensor wires pass exiting the back. In one embodiment the piezo buzzer element is fixed into the mounting block with a shock absorbent silicone bead 50 that offers durability given repeat impact by thousands of objects. In a further embodiment FIG. 5B these sensor blocks are arranged in a linear array mounted on a cross member 59 to form the sensing module 37. In one embodiment Velcro is used to hold sensor blocks in place on the cross member 59. Velcro is preferred because it acts as a shock absorber 57 and helps reduce mechanical vibration from coupling into the sensors, which causes signal noise.

In one embodiment the piezo crystal, 24, FIG. 6A, has an output signal 61 that looks like a damped oscillator. Since the first half cycle of this output is generated while the object is in contact with the sensor this is the portion which best reflects the object's physical properties and of most interest. The preferred embodiment for conditioning the output signal from the piezo crystal 24 is to hook up to network as in FIG. 6B where R1 is greater than R2 creating an asymmetric load impedance. In this embodiment the output signal 61 still oscillates but the oscillations are driven below the reference voltage. This simplifies triggering for the measurement circuit which preferably triggers just once per object impact.

Figure 7A:
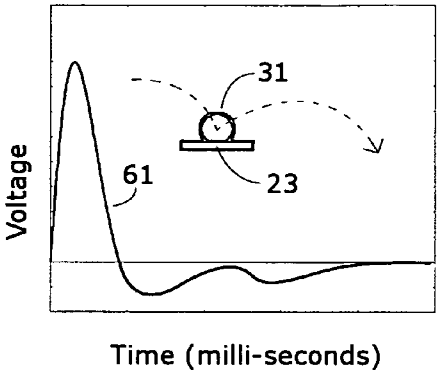
FIG. 7 is a collection of diagrams showing the signals generated by a piezo sensor, how these correlate with the physical properties of an object, and a useful method of making an actuation decision.
Figure 7B:
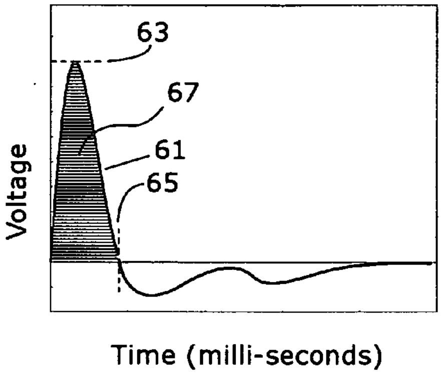
Figure 7C:
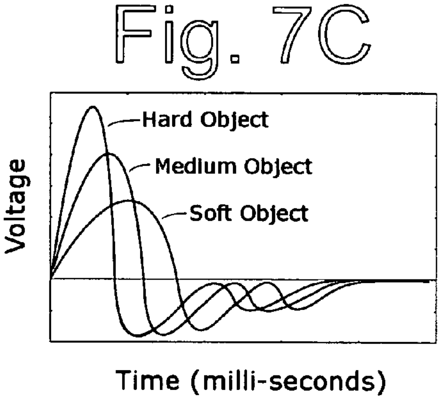

FIG. 7A shows a typical sensor signal 61 generated by a object 31 impacting the sensor surface 23. FIG. 7B identifies the parameters of this signal which are easiest to extract and most useful in determining the physical characteristics of an object having generated that signal. In particular in one embodiment the peak force 63, and contact time 65, can be used to determine appropriately the softness quality of a cranberry. In another embodiment the momentum transferred during the impact corresponds to area of this signal 67. In this embodiment the signal area can be used to infer object mass. FIG. 7C illustrates three signals for three objects of equal weight but different softness. While the area of these three signals is similar the softer the object the lower the peak force and the longer the contact time.

In one embodiment the objects are cranberries and cranberries have a large variation in size. In this embodiment extracting just contact time is not sufficient to do a good job sorting. A much better job can be done if both contact time and peak force are accounted for simultaneously. In the preferred embodiment these two combined logically as in FIG. 7E.

Figure 7D:
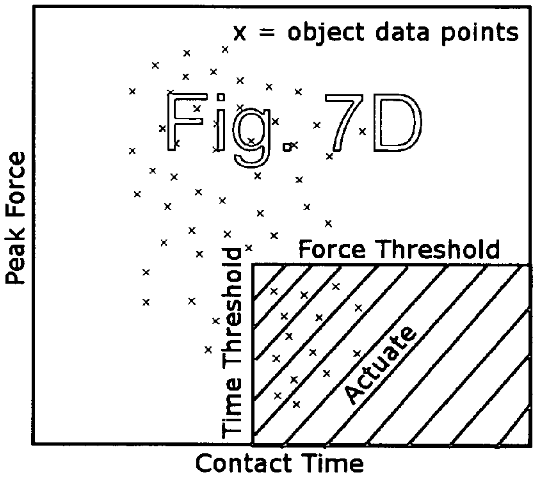
Figure 7E:
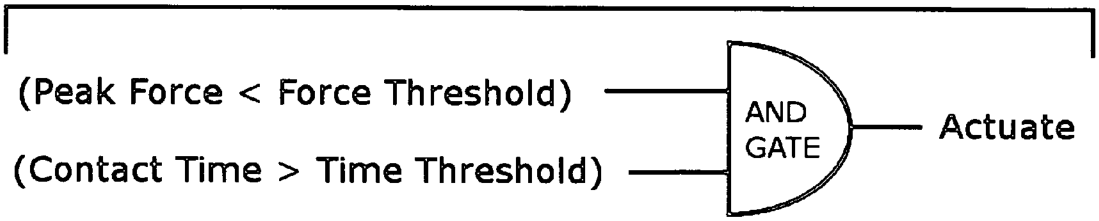

FIG. 7D shows how the logic in FIG. 7E can be displayed visually on a graphical display. This type of display is also the preferred for the interface when adjusting the thresholds during fine tuning of the sorter. In this embodiment it is known that soft objects don't exert peak forces over a certain threshold while hard objects which are also large will sometimes have contact times over the desired minimum threshold required to sort out soft objects of smaller size.

In one embodiment, signals are processed using analog electronic components called op-amps. In this embodiment analog components are used for extracting the values FIG. 7B, 63, 65, 67, from a sensor signal and an actuation decision is made almost instantaneously even before the object leaves the sensing pad.

Figure 8A:
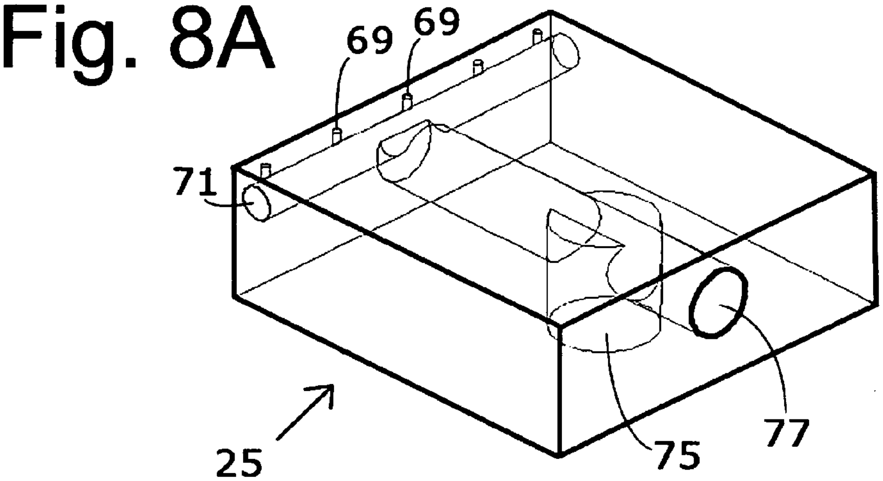
FIG. 8 is a close up diagram showing, by way of example, the air actuation manifold containing multiple air output ports, air valves hooked to the manifold's input port, and these assemblies secured to a cross member, of the system of FIG. 1.
Figure 8B:
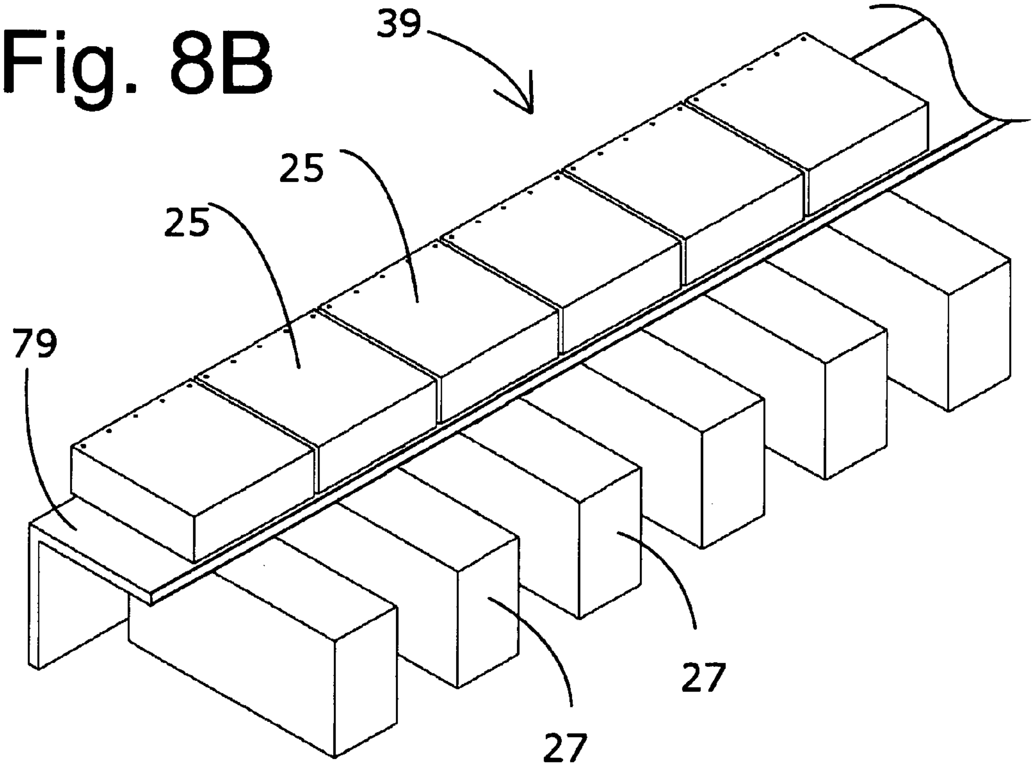

In one embodiment of the actuation system FIG. 8B, 39, the air manifold 25, FIG. 3, FIG. 8A, FIG. 8B has an array of exit ports 69, to span a range of angles over which the object 31 might bounce after impacting the sensor. These air jets are turned on simultaneously by a fast acting pneumatic valve 27 to intercept the object and divert it from its natural path.

In one embodiment FIG. 8A, the air manifold 25 is made from a block of aluminum by drilling blind intersecting holes 69, 71, 75, 77 and then welding the ends shut on 71 and 77. Hole 75 is threaded to mate with the valve 27 using a nipple coupling. In the preferred embodiment the manifold threads onto the valve and then the manifold bolts to the cross member forming the actuation assembly FIG. 8B, 39.

A fast acting pneumatic valve 27 is used to generate the air burst for sorting. The air actuation bar is designed to fit as close to the sensor as possible to minimize the uncertainty in object position between measurement and actuation. Timing of the air jet is achieved by adjusting two parameters called delay and dwell. Delay is how long to wait after measurement before turning on the air pulse. Dwell is how long to leave the air pulse on before turning the air pulse off again.

In one embodiment, mechanical degrees of freedom FIG. 1, 15, 17, 19 for adjusting the relative position of sensors and actuation air manifold are utilized to optimize sorting efficiency within the environmental constraints. The apparatus preferably allows for linear adjustments to be made and restored to within the precision of one millimeter. The apparatus preferably allows for angular adjustments mentioned in this section to be made and restored to within the precision of one degree. For simplicity in implementing the adjustments mentioned below, the apparatus is built such that the sensor surface and the surface of the air actuation bar or manifold are kept permanently in the same plane. The sensor array and the air valve preferably have one radial degree of freedom to also allow for adjusting the distance between the sensors and air actuation bar such that the plastic covering can be fed between the sensors and the air actuation bar, and the gap between sensors and air actuation bar can be temporarily widened for periodic cleaning or maintenance. When the sensor array and the air valve array are locked together as a unit, there is preferably one rotational degree of freedom 19, which allows the unit to rotate about an axis about the center of all the sensors. This embodiment allows the user to change the angle at which objects hit the sensor without changing the location of the sensor center. There are preferably two orthogonal degrees of freedom allowing the unit vertical 15, and horizontal 17, motion.

Figure 9:
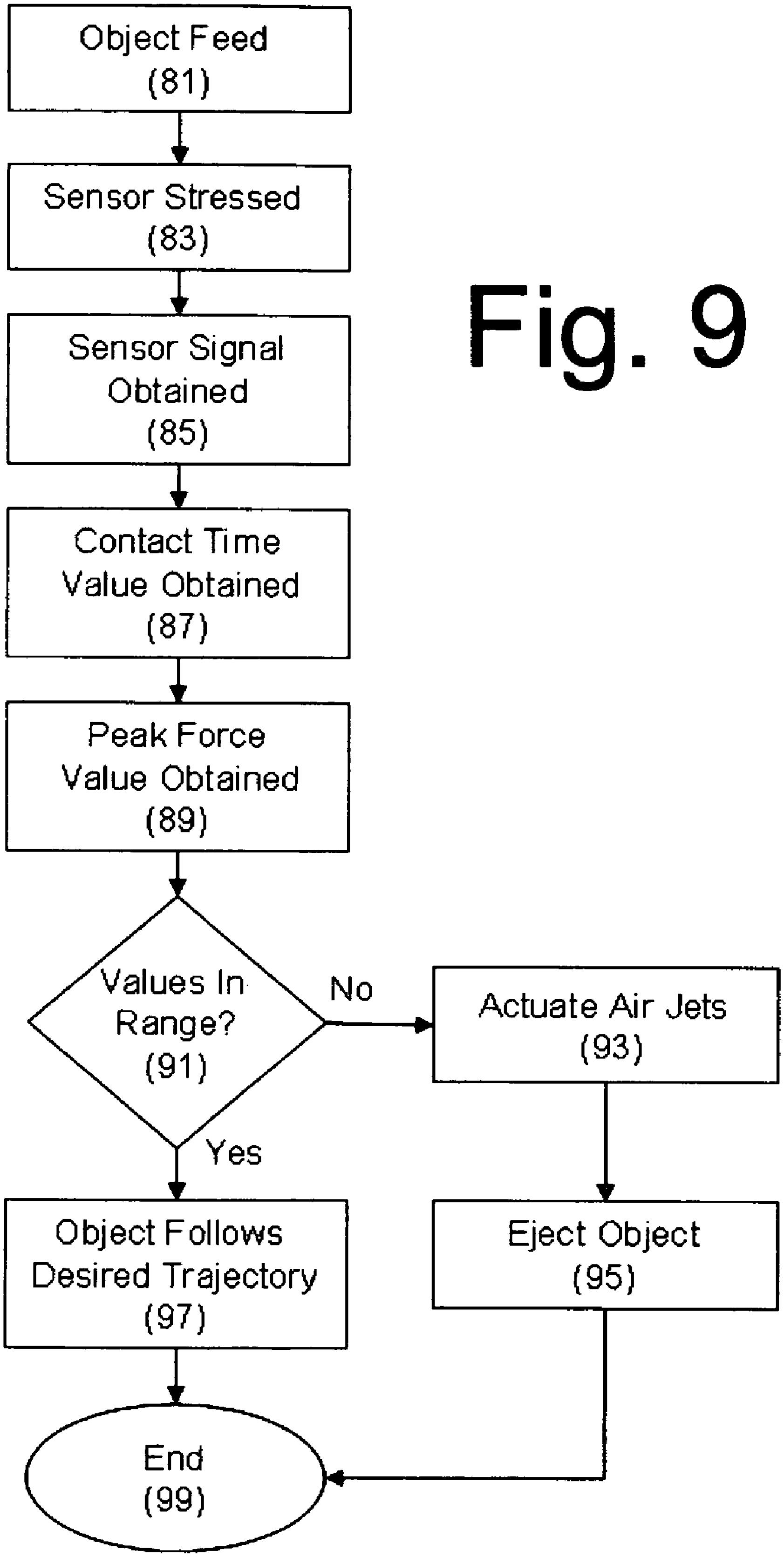
FIG. 9 is process flow diagram showing, by way of example, a method for analyzing signals for an individual object and determining whether to send the object on an off-course trajectory to a different location by way of activated air streams, in accordance with one embodiment.

In one embodiment of the sorting logic a process flow diagram FIG. 9 illustrates how it is decided whether to remove an object from the batch. The object feed 81 delivers an object to the sensor which is stressed by the object's impact 83. The sensor signal is obtained 85, and from the signal a contact time 87 and peak force 89 are extracted. The values are compared to some threshold values to see if they are within range 91. If the values are within range the object follows a desired trajectory 97, if they are not within range the air jet fires 93 to divert the object 95. When this process is finished 99 the cycle begins again.

What is claimed is:

1. A system for automated tactile sorting of objects comprising:

- a delivery module comprising belts, rollers, and a guide comprising base board and fins to form lanes for individually delivering objects to sensing surfaces, each sensing surface corresponding to one lane;
- a plurality of sensor modules, each module comprising the sensing surface where the objects stream from the delivery module to impact and rebound, and a piezo element fastened within a mounting block which is attached to a cross member with a shock absorbent material;
- a protective cover for the sensing surface comprising a covering which can move;
- a signal conditioning module comprising electronic components which transform a sensor output from the sensor module;
- a signal processing module comprising electronic components obtaining, and quantifying values from the sensors output voltage signal;
- a decision module comprising electronic components comparing measured values to threshold values and making an actuation decision;
- a control module comprising a user interface adjusting parameters;
- an actuation module comprising air manifolds redirecting objects;
- means to position the sensor module and the actuation module.

2. A system according to claim 1, wherein the objects are selected from the group comprising of small fruit, berries, cranberries, blueberries, cherries, gooseberries, grapes, cherry tomatoes, grape tomatoes, vegetables, peas, beans, mini kiwi.

3. A system according to claim 1, wherein the delivery module causes a spreading effect in the delivery belt at the delivery point.

4. A system according to claim 1, wherein each fin is placed between two delivery belts.

5. A system according to claim 1, wherein the decision module comprises the values of peak force and contact time for each object impact along with preset thresholds of peak force and contact time to determine the object's softness.

6. A system according to claim 1, wherein the control module is used to change the preset thresholds for peak force and contact time.

7. A system according to claim 1, wherein the actuation module comprises a plurality of air manifolds with multiple air jets per manifold.

8. A system according to claim 1, wherein the means to position the sensor module and actuation module allow moving the sensors into the object stream and also allow the sensors to be rotated relative to the object stream.

9. A method for automated tactile sorting of objects comprising:

- conveying objects in a single file row to a drop off point where the objects are brought into contact one at a time with a tactile sensing surface;
- sensing objects with a stationary tactile sensor where the objects are brought into contact with the tactile sensing surface allowing the objects to rebound naturally, wherein the stationary tactile sensor comprises a piezo element fastened within a mounting block which is attached to a cross member with a shock absorbent material;

protecting the tactile sensing surface with a moveable covering such that a clean sensing surface is maintained by moving a new area of the cover into position over the tactile sensing surface;

conditioning the sensor's output signal wherein the timeframe where each object is in contact with the sensor is analyzed;

measuring, recording, and quantifying attributes of the sensor's output signal corresponding to physical attributes of the object inferred by the sensor to object interaction;

deciding if an object should be removed based on the quantified attributes of the signal correlated with physical properties of the object;

diverting the object and removing the object from the batch.

10. A method according to claim 9, wherein the objects are selected from the group comprising of small fruit, berries, cranberries, blueberries, cherries, gooseberries, grapes, cherry tomatoes, grape tomatoes, vegetables, peas, beans, mini kiwi.

11. A method according to claim 9, wherein the signal measurements are made using analog electronics.

12. A method according to claim 9, wherein the actuation decision is made by comparing objects contact time to threshold time, and comparing objects peak force to threshold force.

13. A method according to claim 9, wherein object measurements are displayed for the user in the context of sorting thresholds so that various methods of adjusting and tuning may be employed.

14. An apparatus for automated tactile sorting of objects comprising:

means for delivering objects one at a time to a sensing surface with a high degree of precision;

a plurality of sensor modules, each module comprising the sensing surface where the objects stream from the delivery module to impact and rebound, and a piezo element fastened within a mounting block which is attached to a cross member with a shock absorbent material;

means for eliminating accumulation of residue and debris at the sensing surface;

means for recording and quantifying values of force exerted by each object impacting the sensing surface and a contact time between each object and the sensing surface;

means for analyzing values of force and contact time for each object correlating with tactile properties of each object and comparing with a predetermined desirable range;

means for determining a destination for each object.

* * * * *